United States Patent
Chiu et al.

(10) Patent No.: US 6,939,521 B1
(45) Date of Patent: Sep. 6, 2005

(54) FLUOROPOLYMER REACTOR WITH HEAT EXCHANGE JACKET

(75) Inventors: Yuon Chiu; William James Hague, both of Morris County, NJ (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 08/975,317

(22) Filed: Nov. 21, 1997

(51) Int. Cl.[7] .............................................. F28D 21/00
(52) U.S. Cl. ...................... 422/203; 422/113; 422/202; 422/205; 422/208; 422/241; 422/242
(58) Field of Search ................................ 422/240, 241, 422/242, 205, 202, 203, 208, 112, 113

(56) References Cited

U.S. PATENT DOCUMENTS

| | | | |
|---|---|---|---|
| 2,768,200 A | | 10/1956 | Busby |
| 2,997,435 A | * | 8/1961 | Millar et al. ................. 376/294 |
| 3,231,338 A | * | 1/1966 | Andrus |
| 3,472,632 A | * | 10/1969 | Hervert et al. ............... 422/242 |
| 3,515,520 A | * | 6/1970 | Hervert ....................... 422/241 |
| 3,949,058 A | * | 4/1976 | Young et al. ................. 423/313 |
| 4,985,208 A | * | 1/1991 | Sugawara et al. ........... 422/135 |
| 5,064,450 A | * | 11/1991 | Lankton et al. .............. 95/211 |
| 5,072,622 A | * | 12/1991 | Roach et al. ................. 73/49.2 |
| 5,246,549 A | * | 9/1993 | Heil ............................... 203/2 |
| 5,552,039 A | * | 9/1996 | McBrayer et al. ............ 210/90 |
| 5,565,393 A | | 10/1996 | Felix et al. .................... 502/20 |
| 5,578,278 A | | 11/1996 | Fall et al. ..................... 422/234 |
| 5,667,758 A | * | 9/1997 | Matsugi et al. .............. 422/198 |
| 5,883,349 A | * | 3/1999 | Kingston ................ 204/157.15 |
| 5,902,912 A | * | 5/1999 | Tung et al. ................... 570/164 |

FOREIGN PATENT DOCUMENTS

| | | |
|---|---|---|
| DE | 43 11 417 A 1 | 10/1994 |
| EP | 0 099 443 | 2/1984 |
| JP | 233102-1995 | 9/1995 |
| JP | WO95/3521 | 12/1995 |

* cited by examiner

*Primary Examiner*—Hien Tran
*Assistant Examiner*—Basia Ridley
(74) *Attorney, Agent, or Firm*—Synnestvedt & Lechner LLP

(57) ABSTRACT

A reactor for fluorinating an organic compound comprising (a) an outer vessel; (b) a reactor vessel being disposed within said outer vessel to define an annular space, said reactor vessel at least partially comprising a fluoropolymer, said annular space being adapted to receive a fluid; (c) at least one pathway for introducing said heating fluid into said annular space; (d) at least one pathway for inputing reaction materials into said reactor vessel; and (e) at least one pathway for ouputing a product stream from said reactor vessel.

16 Claims, 4 Drawing Sheets

FLUOROPOLYMER REACTOR WITH HEAT EXCHANGE JACKET

FIELD OF THE INVENTION

The invention relates generally to a system and method for reacting corrosive materials under pressure. More specifically, the invention relates to a reactor system and method for the liquid-phase fluorination of organic compounds.

BACKGROUND OF THE INVENTION

Liquid-phase fluorination involves a mixture of corrosive reaction materials. The corrosion is acute especially where Lewis-acid catalysts, such as antimony halide catalysts, are used under high reaction pressures and at elevated temperatures. Under these conditions, strong acids form which tend to corrode reactor vessels, even those comprised of corrosion-resistant materials. Reactor corrosion compromises the structural integrity of the reactor and reduces its useful life. Therefore, a need exists to minimize reactor corrosion.

A recent approach to combat reactor corrosion involves lining or coating the inside of the reaction vessel with a fluoropolymer. Although effective in preventing chemical corrosion, the fluoropolymer component of the reactor tends to be problematic, especially for commercial-scale reactors, for example, over 500 gallons. Commonly-encountered problems include body flange seal leakage, liner flexing stresses, hydrogen fluoride permeation through the fluoropolymer liner, and blister formation. Such problems diminish the reactor's durability and lead to premature failure. Additionally, the fluoropolymer component tends to insulate the reactor thermally, necessitating costly and complex external heat transfer means and procedures.

Thus, a need exists for non-corroding reactor systems that can be used for the commercial-scale production of fluorinated compounds where high pressures are encountered and heat transfer is required.

DETAILED DESCRIPTION OF THE INVENTION AND PREFERRED EMBODIMENTS

Figure 1A:
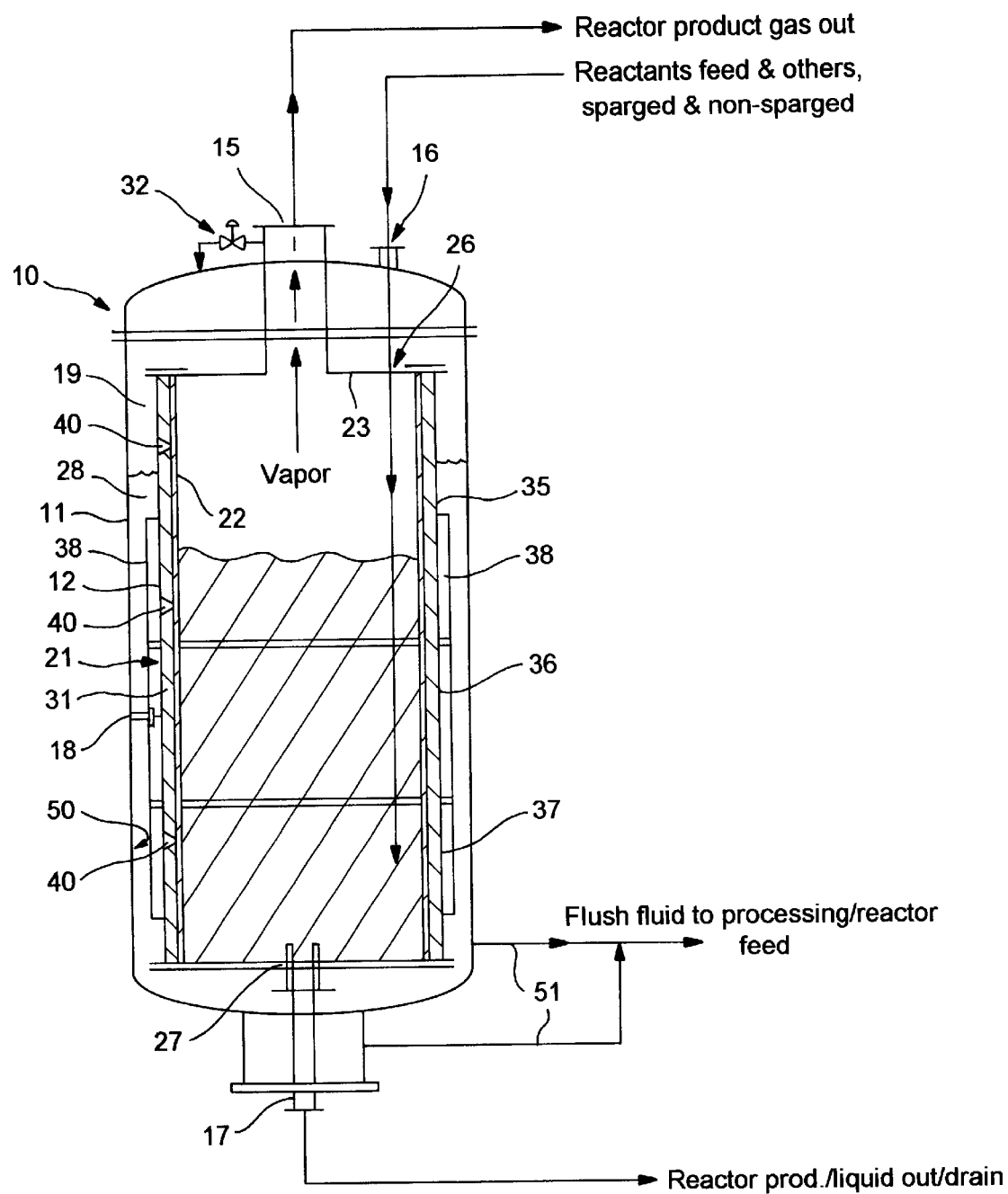
FIGS. 1a and 1b illustrate closed and opened reactor vessel embodiments, respectively, of the reactor system of the invention.

The present invention provides for a chemically-resistant reactor system that is durable and allows for efficient heat transfer. More specifically, the reactor system comprises a fluoropolymer-enhanced reactor vessel contained within a pressure-bearing outer vessel. The configuration of a vessel within another vessel defines an annular space. The combination of the pressure-bearing outer vessel and the annular space facilitates heat transfer and enables the reactor vessel to vent and avoid blistering and other problems associated with fluoropolymer liners.

The reactor apparatus of the present invention facilitates heat transfer several ways. First, the annular space is adapted to contain one or more fluids, either liquid or gas, which may be externally heated or cooled and circulated within the space. The annular space may also be baffled to impart velocity to the fluid to further enhance heat transfer.

In addition to accommodating a heat-transfer fluid, the annular space also allows for a thinner reactor vessel wall which tends to improve heat transfer. More specifically, since the outer vessel is constructed to be the pressure-bearing component of the reactor system, the annular space can be pressured to approximately the reaction pressure. This results in near-pressure equalization on either side of the reactor vessel wall. Consequently, the reactor vessel wall does not encounter forces from high pressure differentials and can be constructed with relatively thin walls or it can be constructed totally of a fluoropolymer despite the fluoropolymer's marginal strength.

The annular space not only provides means of conveniently heating or cooling the reaction, but also improves the reactor vessel's useful life. In a preferred embodiment, the reactor comprises a rigid member and a loose, fluoropolymer liner. The rigid member has weep holes to allow those reactants that permeate the fluoropolymer-lined reactor to vent. This prevents reactants from building up between the liner and the reactor wall and forming blisters or otherwise leading to liner failure. Such a configuration therefore improves the reactor vessel's durability and extends its useful life.

The annular space accommodates a fluid which flushes away reaction materials escaping from the reactor vessel, and, when pressurized to approximate reaction pressure, the fluid relieves the stress on the fluoropolymer liner spanning the weep hole. Additionally, the fluid in the annular space is easily monitored to detect the existence of a leak. In a preferred embodiment, the fluid used to both impart heat and capture escaping reactants is a starting material which is fed into the reactor after circulating about the annular space. This way, the errant reactants are returned the reactor.

Therefore, in accordance with the present invention, a commercial-scale reactor may be designed more for corrosion resistance than for strength because the pressure-bearing outer vessel relaxes the structural demands on the reactor vessel. The present invention is especially useful for the liquid-phase fluorination of chlorinated hydrocarbons in which the reaction is very corrosive to conventional metal reactors. However, the system also may be useful for other processes, which may not be particularly corrosive, but would benefit from improved heat transfer and/or leak detection.

One aspect of the invention is a reactor. In a preferred embodiment, the reactor comprises: (a) an outer vessel; (b) a reactor vessel being disposed within said outer vessel to define an annular space, said reactor vessel at least partially comprising a fluoropolymer, said annular space being adapted to receive a fluid; (c) at least one pathway for introducing said fluid into said annular space; (d) at least one pathway for inputing reaction materials into said reactor vessel; and (e) at least one pathway for ouputing a product stream from said reactor vessel.

Another aspect of the invention is a method for producing a compound using the reactor. The process comprises: (a) providing a reactor of the present invention; (b) feeding said reactor vessel with reaction material; (c) reacting said reaction materials to produce said compound by operating said reactor vessel at one or more reaction pressures and at one or more reaction temperatures; and (d) regulating said one or more reaction temperatures by introducing either a heated or cooled fluid into said annular space.

Figure 1B:
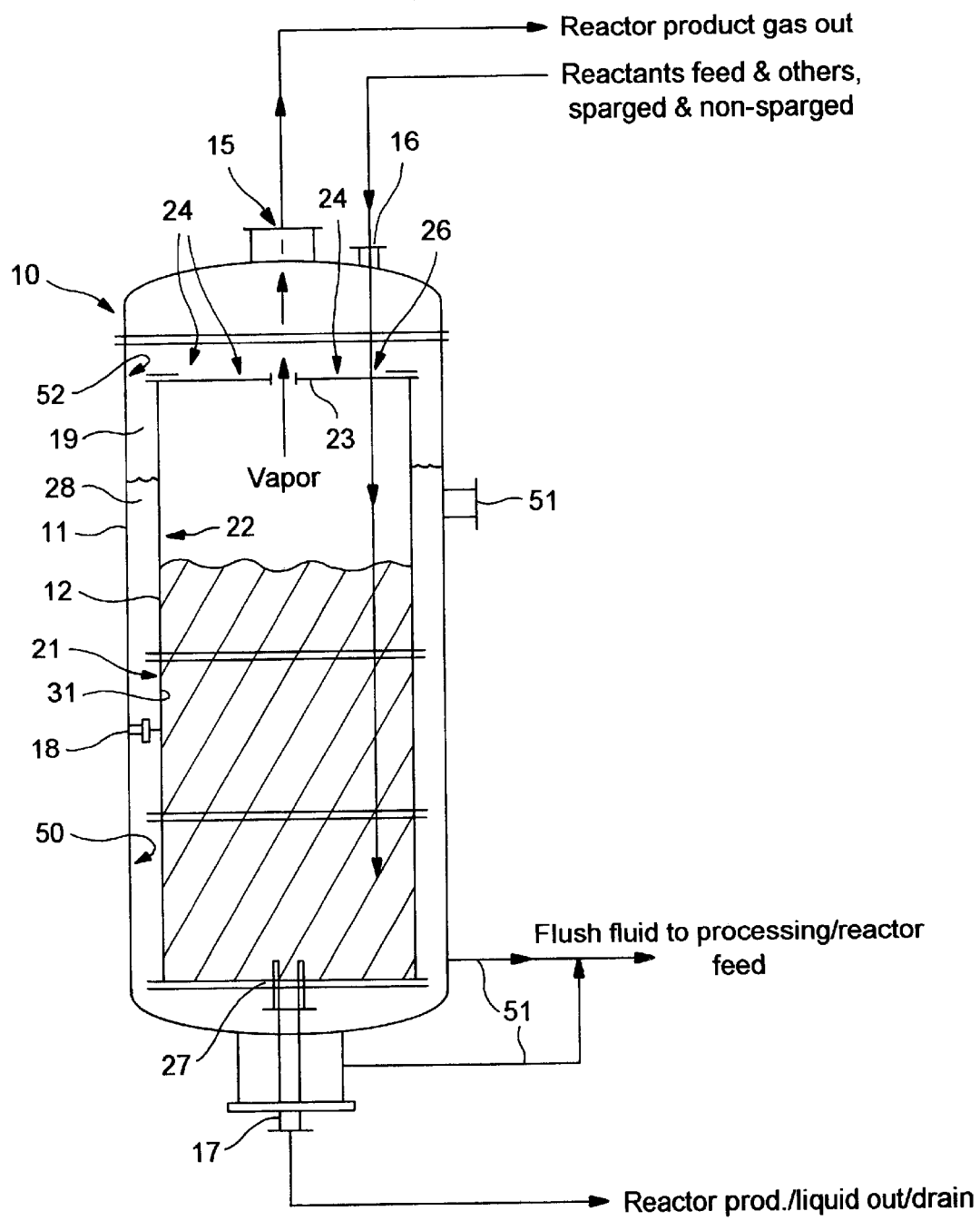

Referring now to FIGS. 1a & 1b, preferred embodiments of the reactor apparatus 10 is shown. The reactor apparatus 10 comprises a reactor vessel 12 contained by an outer vessel 11. As shown, the outer vessel 11 includes an inlet 16 for the introduction of reaction materials, an outlet 15 for the removal of the product vapor stream, and an outlet 17 for the removal of the reaction liquid stream. Outer vessel 11 has a size and shape suitable to enclose reactor vessel 12, which is supported within outer vessel 11 by supporting means 18. Reactor vessel 12 has a top 23 which has an inlet 26 through which reaction feed materials are introduced. Reactor outlet 27 permits withdrawal of a liquid stream from reactor vessel 12. Reactor outer surface 21 and vessel inner surface 50 define annular space 19. The annular space accommodates a fluid that can heat or cool the reactor vessel, and that can absorb and flush away reaction materials that leak from the reactor. The outer vessel 11 comprises an inlet/outlet 51 for introducing or removing fluid from the annular space.

The outer vessel 11 is designed as the pressure containing component of the system. It therefore should be structurally suited for expected operating pressures. The outer vessel is designed preferably to withstand pressures of at least about 50 psig, more preferably of at least about 100 psig, and still more preferably of at least about 160 psig. The construction requirements for such pressurized vessels is well known in the art.

The outer vessel 11 may be constructed of any conventional material used for liquid-phase fluorination reactors, such as corrosion resistant metals or fluoropolymers. Suitable metals include, without limitation, cold rolled steel, carbon steel, INCONEL™, HASTELLOY™, and the like. In the preferred embodiment, the vessel is made of carbon steel for economic reasons. Additionally, a portion of the vessel may be lined with a fluoropolymer as discussed below in regard to the reactor vessel 12.

Reactor vessel 12 is designed primarily to be non-corroding and commercially viable. It is not designed as a high-pressure containment for the reaction. Consequently, it can be comprised of a fluoropolymer which imparts excellent chemical resistance, although marginal strength. As used herein, the terms "fluorinated polymer" and "fluoropolymer" are used interchangeably and broadly refer to any polymer, copolymer or blend of polymers having a fluoride atom in at least one of the monomers. Preferred materials include, for example, polytetrafluoroethylene, poly(vinylidene fluoride), ethylene-tetrafluoroethylene polymer, ethylene-hexafluoropropylene polymer, tetrafluoroethylene-hexafluoropropylene polymer, perfluoroalkoxy polymer, any modified version of the above-mentioned polymers, and blends of two or more thereof. Polytetrafluoroethylene or its modified version is more preferred.

The reactor vessel 12 may be comprised totally of a fluoropolymer or its interior surface 22 may be lined or coated with a fluoropolymer. Where reactor vessel 12 is constructed entirely of fluoropolymer, the reactor wall preferably has a thickness of from about 25 to about 100 mm, although any thickness may be used within the scope of the invention. In the preferred embodiment, however, reactor vessel 12 is made of a rigid member 31 having its interior surface coated or lined with a fluoropolymer 22a (shown in FIG. 1a only). The rigid member 31 is typically constructed of a metal such as, for example, cold rolled steel, carbon steel, INCONEL™, HASTELLOY™, and the like. Preferably, the vessel is made of carbon steel for economic reasons since corrosion protection is provided by the fluoropolymer liner. With such a configuration, the metal wall thickness is between about 3 to about 6 mm and the fluoropolymer thickness is between below about 1 to about 35 mm, preferably from about 1 to about 6 mm.

In a more preferred embodiment, the fluoropolymer component of the reactor vessel is a loose fluoropolymer liner. The term "loose fluoropolymer liner" broadly refers to a liner which covers at least portion of metallic part of the reactor and which is fitted from a film or sheet of a fluoropolymer material. Such a liner provides a reactor with a chemically-resistant barrier that is more durable then molded-type, fluoropolymer liners. More specifically, a loose liner tends to be less porous than a molded liner and, thus, tends to maintain a seal for a longer time. Preferably, the sheet has a thickness of no less than about 0.7 mm which is thicker generally than most molded liners.

Also in the more preferred embodiment, the reactor wall has at least one weep hole 40 (shown in FIG. 1a only), and preferably a plurality of weep holes 40. Weep holes allow reactants that permeate the liner to vent into the annular space. This way, pressure does not build up between the rigid member and the liner and cause blisters. The number and size of the weep holes may vary according to reactor size and other variables, although a weep hole having a diameter from about ⅛ to about ½ inch is generally preferred. A reactor having one or more weep holes requires that the liner have adequate strength to span the weep hole under reaction pressures. However, since the annular space can be pressurized to near reaction pressure, the resultant pressure on the fluoropolymer liner is very little.

Reactor top 23 may be closed or opened, as shown in FIGS. 1a & 1b respectively. As shown in FIG. 1a, the reactor vessel has a closed top such that the contents of reactor vessel 12 do not enter annular space 19. In closed reactor vessel embodiments, a pressure balancing device 32 is preferable. The pressure balancing device 32 would typically be a pressure differential control valve.

Pressure balancing is desirable for two reasons. First, if a significant difference develops between the pressures of the reactor and the annular space, then the reactor needs to be constructed to withstand that differential. This results in an increase in the reactor wall thickness. For example, to withstand full operating pressure of 160 psig, the reactor wall must be several times thicker than the preferred thickness of 3 to 6 mm. A thicker reactor wall, of course, decreases the heat transfer efficiency. Second, if the annular space pressure were higher than the reactor's, then there would be no force driving the reactant through the weep holes of the reactor and into the annular space. On the contrary, the fluid may even enter the weep holes and cause the liner to blister thereby magnifying the problems weep holes are designed to prevent.

It is therefore preferable to maintain a slight positive pressure in the reactor relative to the annular space. The pressure in the annular space should be about 0.1 to about 25 psig lower than the reactor. The pressure in the reactor vessel 12 can be a negative or positive pressure relative to atmospheric, but preferably positive.

An opened reactor vessel 12, as shown in FIG. 1b, contains one or more outlets 24 permitting the flow of gaseous reaction materials, products and byproducts from reactor vessel 12 into annular space 19. Since the gaseous product stream tends to contain only small amounts of Lewis acid catalyst, it is not particularly corrosive. Nevertheless, in the event the liquid reactants overflow the reactor or just for extra corrosion protection, it is preferable to coat or line the upper space 52 of the inner surface 50 of the outer vessel 11 with a fluoropolymer.

Reactor vessel 12 may be of any desired size, however, to be commercially viable, it should be at least about 500 gallons, and preferably at least 1000 gallons. Such capacities are possible using a loose, fluoropolymer liner, which requires no special equipment for installation, such as a large rotary oven. Moreover, the durability of such large reactors is improved by the weep holes which prevent blisters from forming.

Reactor vessel 12 may be constructed by any convenient means known in the art. It may be preferable for reactor vessels larger than about 1000 gallons to be segmented. For example, reactor vessel 12 may be constructed of top 35, middle 36, and bottom 37 segments which are connected together with any suitable connecting means such as by bolting flanges of each segment together.

Furthermore, heat transfer may be further increased by providing reactor vessel 12 with fins 38 or rods which increase the surface area available for heat transfer. For example, the fins 38 or rods may be welded or attached to the outside surface of the reactor vessel such that they extend into the annular space. Such fins or rods may even be configured to act as baffles as described below.

The disposition of the reactor vessel within the outer vessel defines an annular space. The annular space facilitates heating the reactor, contains reaction materials leaking from the reactor vessel, and substantially equalizes reactor pressure.

Annular space 19 contains fluid 28 that may be heated to supply heat to reactor vessel 12. Fluid 28 may be heated or cooled by any conventional means, such as a heat exchanger, and then circulated into annular space 19. Preferably, in order to increase the rate of heat transfer between fluid 28 and reactor vessel 12, a means for increasing the velocity of fluid 28 in annular space 19 is provided. Suitable means include, without limitation, baffles, paddles and circulating pumps.

Figure 2:
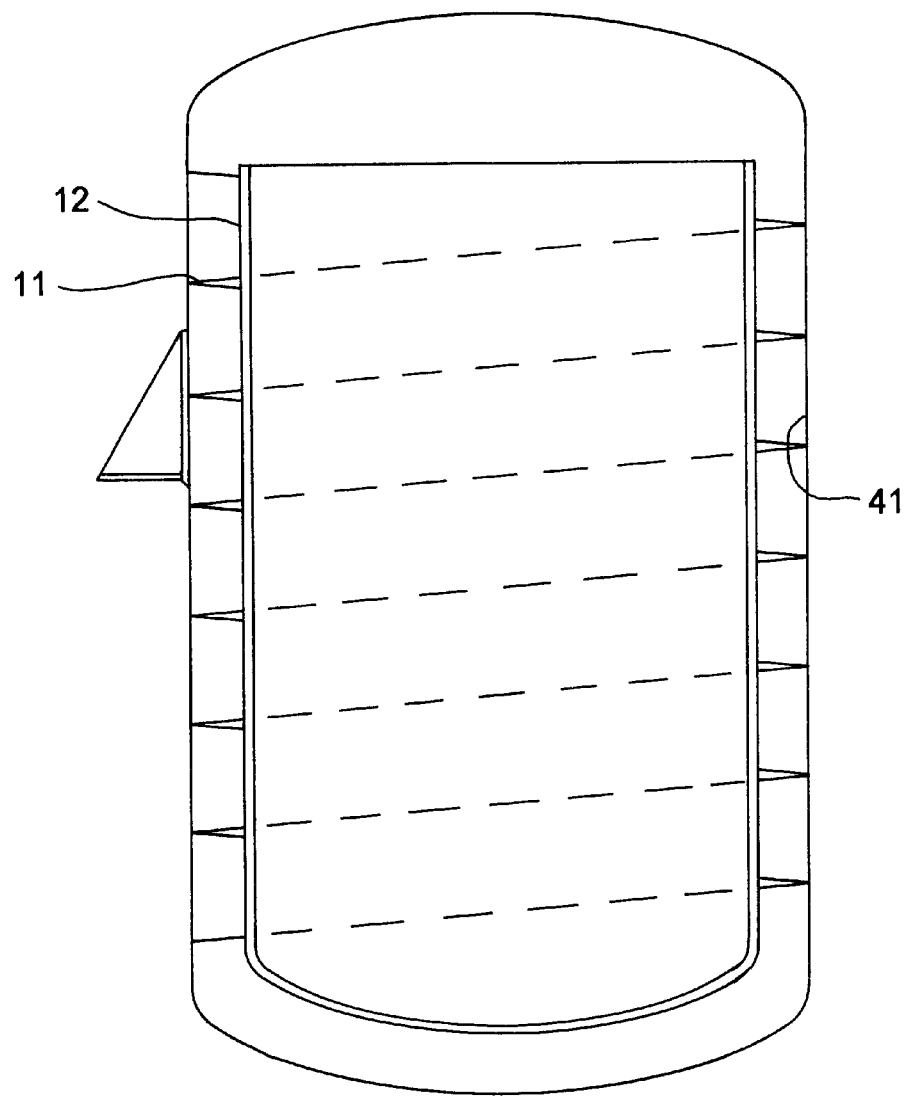
FIG. 2 illustrates an embodiment of the baffling means of the reactor system of the present invention.
Figure 3:
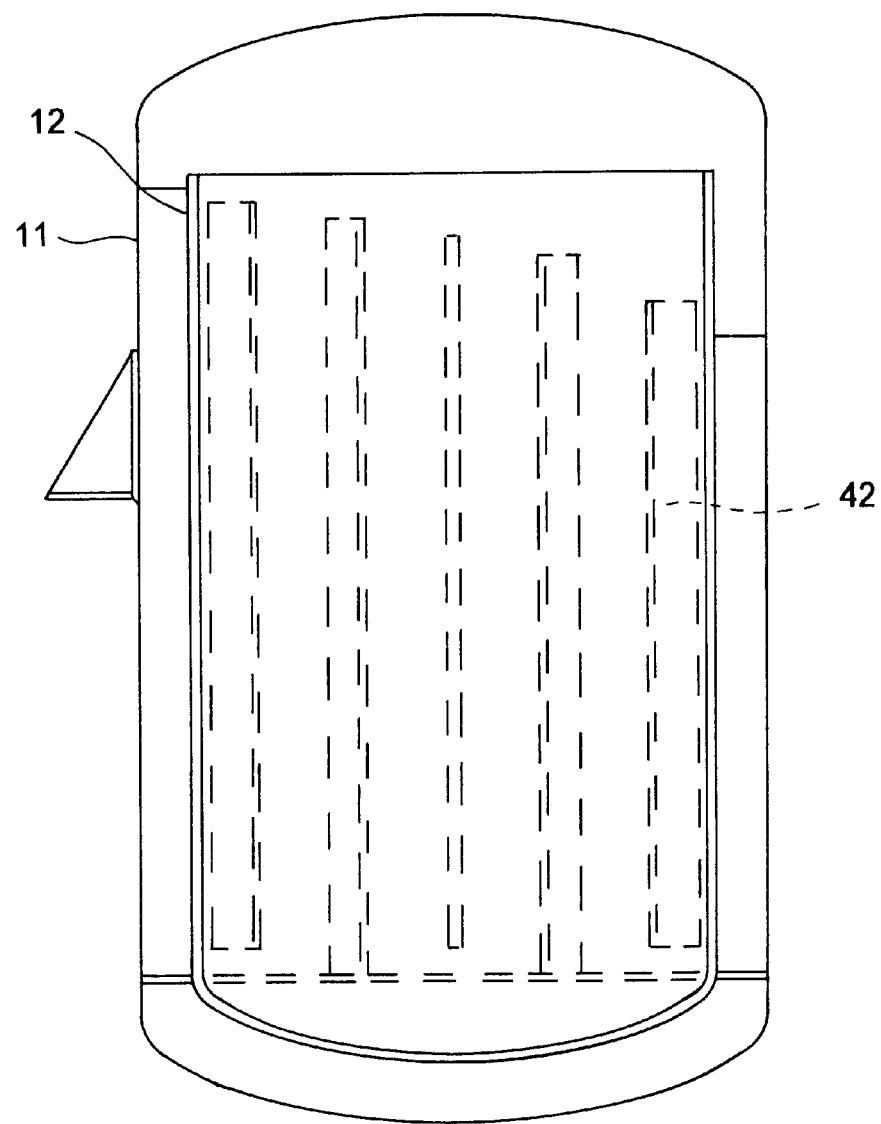
FIG. 3 illustrates another embodiment of the baffling means of the reactor system of the present invention.

FIGS. 2 and 3 depict alternative velocity increasing means. FIG. 2 depicts a spiral baffle 41, and FIG. 3 depicts cascade baffles 42. As mentioned above, the baffles also increase available surface area to improve heat transfer between the reactor vessel and the fluid. To construct such baffles, one edge of the baffle may be welded onto the outside surface of the reactor vessel. Once the reactor vessel is inserted into the outer vessel, the other baffle edge will loosely fit against the inner wall of the outer vessel. Other construction techniques will be apparent to those skilled in the art.

The annular space also is useful for flushing away leaks from the reactor vessel. In a preferred embodiment, the reactor apparatus is designed to accommodate leaks of reaction materials, such as hydrogen fluoride, through the reactor fluoropolymer. More specifically, a free-standing fluoropolymer film is provided along reactor inner surface 22 and weep holes 40 are provided in reactor wall. Any reactant leaking through the fluoropolymer will be absorbed or otherwise flushed away by fluid 28 in annular space 19. In a more preferred embodiment, a hydrogen fluoride sensor is provided to detect the presence and concentration of one or more reaction materials, such as hydrogen fluoride, in annular space 19. Any suitable sensor may be used such as an optical sensor.

The type of fluid used in the annular space depends upon the user's preference and heating/cooling requirements. Suitable fluids range from relatively inert substances, such as oils and glycols, to starting materials for the reaction, such as organic compounds. In the preferred embodiment, the fluid is a starting material which is subsequently fed into the reactor. This way, the fluid imparts heat to the reactor externally when circulating and internally when fed to the reaction. Moreover, any reactants which leak through the reactor that are absorbed by the fluid are returned to the reactor when the fluid is fed to the reaction.

The size of the annular space 19 also depends upon the preference of the user. A narrower annular space provides for better heat transfer, but is more difficult to construct. Therefore, in practice, it is a compromise between heat transfer efficiency and construction complexity. A typical width ranges from about 50 to about 200 mm, preferably from about 100 to about 150 mm.

The apparatus of the invention is well suited for reactions in which corrosive starting materials, catalysts, by-products, or products are involved. Moreover, the apparatus is particularly well suited where high temperatures and pressures are required. One such reaction is the liquid-phase fluorination of an organic compound to produce a fluorinated product. In such a process, the reaction materials, which include an organic starting material, a fluorinating agent, and a fluorinating catalyst, are charged to reactor vessel 12 via inlets 16 and 26. Alternatively, as described above, the organic starting material may first be circulated in the annular space to impart heat to reactor and absorb leaks, and then fed into the reactor to exploit its remaining heat, to return errant reaction materials, and to feed the reaction.

The organic starting material may be any compound containing a carbon-bonded chlorine or other atom replaceable by fluorine and/or that may contain a carbon-carbon unsaturated bond that is saturatable with fluorine. Illustrative organic starting materials include, without limitation, chlorinated hydrocarbon compounds containing from 1 to 6 carbon atoms and 1 to 12 chlorine atoms. Preferred organic starting material compounds have the formula $CF_yCl_{3-y}CH_2CHF_wCl_{2-w}$, wherein w=0 or 1, and y=0–3 (see also, U.S. Pat. No. 5,574,192).

Suitable fluorination agents include any material which provides fluorine for the fluorination reaction. Preferred fluorination agents include, for example, hydrogen fluoride, elemental fluorine, $BF_3$, antimony pentafluoride. The more preferred fluorination agent is hydrogen fluoride.

Any suitable fluorination catalyst may be used including, without limitation antimony, arsenic, niobium, tin, titanium, and tantalum halide catalysts. Examples of these catalysts include, without limitation: pentavalent antimony, niobium, arsenic and tantalum halides; pentavalent antimony, niobium, arsenic and tantalum mixed halides; and mixtures of pentavalent antimony, niobium, arsenic and tantalum halide catalysts. Pentavalent antimony, niobium, arsenic and tantalum halides are commercially available, and mixed halides thereof are created in situ upon reaction with hydrogen fluoride (see U.S. Pat. No. 5,574,192). Antimony pentachloride is more preferred due to its low cost and availability. Pentavalent antimony mixed halides of the formula $SbCl_2F_3$ and $SbBi_2F_3$ where n is 0 to 5 are most preferred. Although the amount of fluorination catalyst used may vary widely, the weight percent of catalyst relative to the organic starting material generally ranges from about less than 1 to about 75%, preferably from about 5 to about 50%, and more preferably from about 10 to about 25%.

It may be advantageous to periodically regenerate the catalyst which may be accomplished by any means well known in the art. For example, the catalyst may be regenerated by adding chlorine, in an amount from about 1 to about 10 mole percent relative to the amount of catalyst initially present in the reactor, to the combination stream of organic starting material and the recycled stream of underfluorinated materials and hydrogen fluoride. The chlorine may be continuously or intermittently added. One of ordinary skill in the art can readily determine the amount of chlorine to be added in order to optimize the use of the catalyst.

The organic starting material is preheated, preferably outside the reactor to a temperature of from about ambient to about 350° F. The organic starting material may be used as fluid 28 which is circulated in annular space 19, in which case the organic material is reheated to a temperature just below the temperature at which the compound breaks down so as to impart the maximum heat via heat exchange to the reaction mixture. For example, in the case of using G240fa as the organic starting material, the preheat temperature is likely to be limited to about 250° F. to minimize breakdown. Absent thermal breakdown, higher temperatures are preferred up to about 350° F. which is just below the thermal property limits of many fluoropolymer components.

Reaction pressure can vary and optimal pressures can be determined by someone skilled in the art without undue experimentation. Convenient operating pressure range from about 30 to about 300 psig, preferably from about 70 to about 260 psig, and more preferably from about 100 to about 200 psig. As mentioned above, the pressure in the annular space preferably should be less, and preferably about 0.1 to about 25 psig below the reaction pressure to maintain the reactor at a slight positive pressure.

The reaction temperature generally is from about ambient to about 350° F., preferably from about 100 to 200° F. Heat can be supplied either by introducing superheated HF at about 200 to about 400° F., or by circulating fluid 28 at least partially in the annular space at an initial temperature of about 200 to about 400° F., and preferably about 250 to 350° F.

Reaction times are dependent on several factors including catalyst concentration, the type of catalyst, and the temperature. For a batch process, the progress of the reaction can be monitored conveniently by the increase in pressure due to the formation of by-product HCl. Typical reaction times range from about 1 to about 25 hours, and preferably from about 2 to about 8 hours. For a continuous process, the reaction times ranges from about 1 second to about 5 hours, and, preferably, from about 10 seconds to about 1 hour.

The fluorination reaction provides a product stream from which the fluorinated product is recovered. In a preferred embodiment, the fluorinated product is recovered by distillation techniques well known in the art.

The invention will be clarified further by a consideration of the following non-limiting example.

EXAMPLE 1

This example illustrates the production of 1,1,1,3,3-pentafluoropropane (245fa), which is highly corrosive, in a 2000 gallon reactor vessel, which is generally considered viable for commercial-scale production.

The reaction apparatus used comprised a 2000 gallon steel reactor vessel lined with a loose, 3 mm thick PTFE sheet, and a 3000 gallon outer vessel which supported and enclosed the reactor vessel. To the reactor vessel were introduced: $C_3H_3Cl_5$ in the liquid phase, at a temperature of 200° F., at pressure of 160 psig, and at rate of about 4500 lb/hr; and HF at a temperature of 350° F., at pressure of 160 psig, and at rate of 3300 lb/hr. The reactor vessel was pre-charged with 10,000 lb of antimony pentachloride catalyst.

The product, 245fa (2700 lb/hr), along with HCl (3500 lb/hr) and unreacted starting material (about 1500 lb/hr) were removed in a gaseous product stream and separated using conventional distillation techniques.

What is claimed is:

1. A reactor for fluorinating an organic compound comprising:
   an outer vessel;
   a reactor vessel having a reactor wall which defines an inner volume, said reactor vessel being disposed within said outer vessel to define an annular space between the reactor wall and said outer vessel such that said inner volume and said annular space are separated only by said reactor wall, said reactor wall comprising a rigid member having an interior surface which is at least partially lined with a fluoropolymer liner, said rigid member having at least one weep hole, which is in fluid communication with said annular space but which does not penetrate through said liner;
   wherein said annular space receives a fluid for effecting heat transfer across said reactor wall;
   wherein said outer vessel is rated for higher pressure than said reactor vessel;
   at least one pathway for introducing said fluid into said annular space;
   at least one pathway for inputting reaction materials into said reactor vessel;
   at least one pathway for outputting a product stream from said reactor vessel; and
   wherein said reactor has either a first configuration or a second configuration to equalize pressure between said inner volume and said annular space such that said pressure rating of said reactor vessel is not exceeded and such that pressure in said annular space is no greater than pressure of said inner volume, in said first configuration said annular space and said inner volume are in fluid communication, in said second configuration said inner volume is fluidly isolated from said annular space and said reactor further comprises a pressure balancing device to regulate pressure differential between said inner volume and said annular space.

2. The reactor of claim 1, wherein said fluoropolymer liner has a thickness of from below about 1 to about 6 mm and wherein said rigid member has a thickness of about 3 to about 6 mm.

3. The reactor of claim 1, wherein said reactor further comprises baffles in said annular space.

4. The reactor of claim 3, wherein said baffles are configured as heat transfer members.

5. The reactor of claim 1, wherein said reactor has said first configuration and said reactor vessel is open to said annular space.

6. The reactor of claim 5, wherein said outer vessel is at least partially lined with a fluoropolymer.

7. The reactor of claim 1, wherein said reactor vessel has a capacity of at least 500 gallons.

8. The reactor of claim 1, further comprising:
   leak detection means for monitoring said fluid to detect presence of one or more of the reaction materials.

9. The reactor of claim 1, wherein said reactor has said second configuration and wherein said pressure balancing device comprises a regulator valve suitable for equalizing pressure between said inner volume and said annular space such that pressure of said inner volume is about 0.1 psig to about 25 psig above that of said annular space.

10. The reactor of claim 9, wherein said reactor has said second configuration.

11. A reactor for fluorinating an organic compound comprising:

an outer vessel having a pressure rating of at least 50 psig;

a reactor vessel having an inner volume for facilitating pressurized reactions, said reactor vessel having a pressure rating less than that of said outer vessel and being disposed within said outer vessel to define an annular space, said annular space receiving a fluid, said reactor vessel comprising a reactor wall having a rigid member having an interior surface at least partially lined with a fluoropolymer liner, said rigid member having at least one weep hole which is in fluid communication with said annular space but which does not penetrate through said liner;

at least one pathway for introducing said fluid into said annular space, wherein said annular space is pressurized with said fluid to the extent that pressure differential across said reactor wall does not exceed the pressure rating of said reactor vessel;

at least one pathway for inputting reaction materials into said reactor vessel;

at least one pathway for outputting a product stream from said reactor vessels; and wherein said reactor has either a first configuration or a second configuration to equalize pressure between said inner volume and said annular space such that the pressure rating of said reactor vessel is not exceeded, in said first configuration said annular space and said inner volume are in fluid communication, in said second configuration said inner volume is fluidly isolated from said annular space and said reactor further comprises a pressure balancing device to regulate pressure differential between said inner volume and said annular space.

12. The reactor of claim 11, wherein said reactor has said second configuration and wherein said pressure balancing device comprises a regulator valve suitable for equalizing pressure between said inner volume and said annular space such that pressure of said inner volume is about 0.1 psig to about 25 psig above that of said annular space.

13. The reactor of claim 11, wherein said fluoropolymer liner has a thickness of from below about 1 to about 6 mm and wherein said rigid member has a thickness of about 3 to about 6 mm.

14. The reactor of claim 11, further comprising:

leak detection means for monitoring said fluid to detect presence of one or more of the reaction materials.

15. The reactor of claim 11, wherein said reactor vessel has a capacity of at least 500 gallons.

16. The reactor of claim 11, wherein said reactor comprises baffles disposed in said annular space wherein said baffles are configured as heat transfer members.

* * * * *